United States Patent
Settle

[19]

[11] Patent Number: 6,026,811
[45] Date of Patent: Feb. 22, 2000

[54] PROTECTIVE COVER FOR NASAL AIR SUPPLY HOSE

[76] Inventor: Romaine A. Settle, 4224 Massachusetts St., Long Beach, Calif. 90814

[21] Appl. No.: 09/042,183

[22] Filed: Mar. 12, 1998

[51] Int. Cl.[7] .................................................. A61M 16/00
[52] U.S. Cl. .............................. 128/207.17; 128/207.18; 128/DIG. 26
[58] Field of Search ............................. 128/864, 206.11, 128/207.17, 207.18, DIG. 26

[56] References Cited

U.S. PATENT DOCUMENTS

| | | | |
|---|---|---|---|
| 3,146,778 | 9/1964 | Krawiec | 128/DIG. 26 |
| 3,430,300 | 3/1969 | Doan | 128/DIG. 26 |
| 3,513,844 | 5/1970 | Smith | 128/207.18 |
| 3,713,448 | 1/1973 | Arrott | 128/207.17 |
| 3,802,431 | 4/1974 | Farr | 128/207.18 |
| 4,535,767 | 8/1985 | Tiep et al. | 128/207.18 |
| 4,699,139 | 10/1987 | Marshall et al. | 128/207.18 |
| 4,739,757 | 4/1988 | Edwards | 128/207.18 |
| 4,827,923 | 5/1989 | Bishop et al. | 128/206.11 |
| 4,949,733 | 8/1990 | Sampson | 128/864 |
| 5,025,805 | 6/1991 | Nutter | 128/207.18 |
| 5,068,931 | 12/1991 | Smith | 5/84 |
| 5,193,106 | 3/1993 | Desena | 378/163 |
| 5,335,659 | 8/1994 | Pologe | 128/207.18 |
| 5,400,776 | 3/1995 | Bartholomew | 128/207.18 |
| 5,438,979 | 8/1995 | Johnson, Jr. et al. | 128/DIG. 26 |
| 5,709,665 | 1/1998 | Vergano et al. | 128/DIG. 26 |

*Primary Examiner*—Aaron J. Lewis
*Attorney, Agent, or Firm*—Fulwider Patton Lee & Utecht, LLP

[57] ABSTRACT

The invention is a method for use and a protective cover apparatus for ear-mounted nasal air supply hoses which prevents skin discomfort, irritation, blisters, abrasions, pressure sores and other injuries and which promotes healing of such irritation, injuries and sores. The invention incorporates a generally rectangular, elongated strip of flexible fabric which is wrapped around a segment of the air supply hoses and fastened along confronting margins on opposing edges of the strip. The flexible fabric strip incorporates an outer cover of lambs wool or similar material for protecting the skin and an inner padding of slightly adhesive or high-friction material, such as a thin layer of latex rubber or releasable adhesive to inhibit longitudinal movement of the protective cover along the air hose. The strip of material is supplied in either pre-cut lengths of a predetermined size or a roll for easy dispensing and convenient storage. The protective cover also incorporates a plurality of pairs of release tabs extending from the opposing edges which are pulled apart to facilitate removal of the cover from the air hose. The pairs of release tabs are spaced apart on the uncut roll of material at predetermined intervals and in such numbers such that at least one pair of release tabs are present on the protective cover for easy removal.

19 Claims, 3 Drawing Sheets

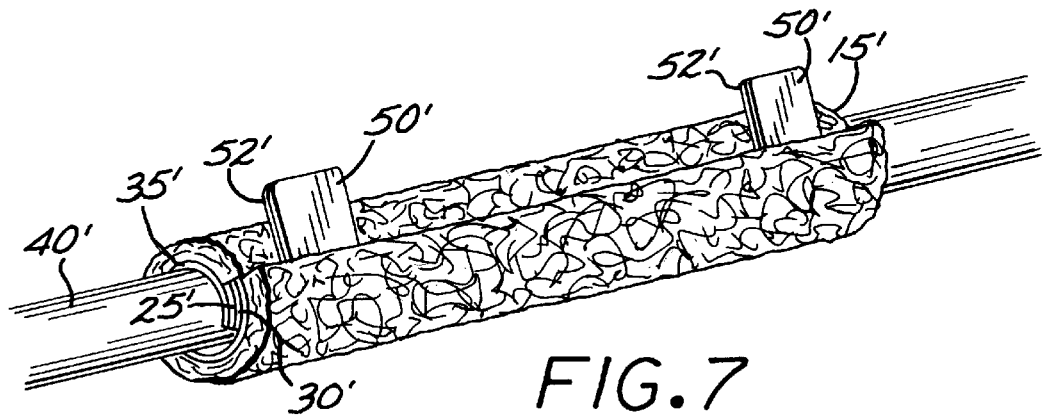
FIG. 7
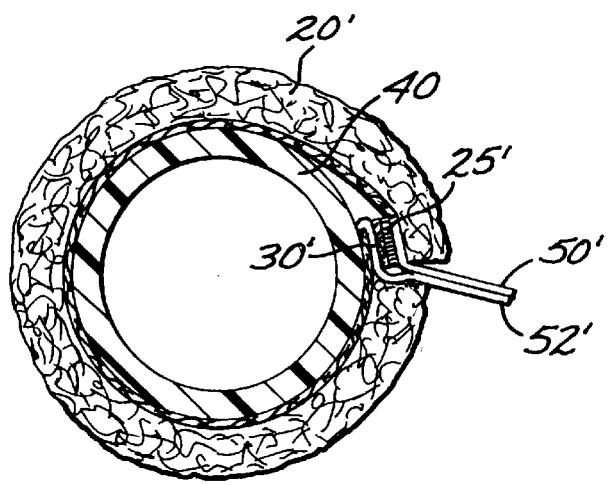
FIG. 8
FIG. 9
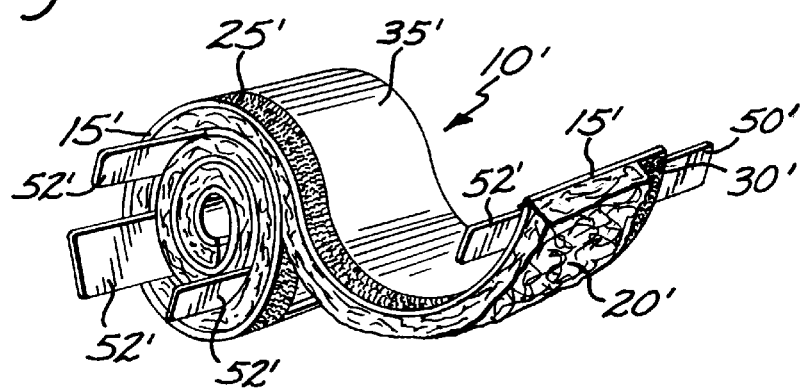

PROTECTIVE COVER FOR NASAL AIR SUPPLY HOSE

BACKGROUND OF THE INVENTION

1. Field of the Invention

This invention relates to a cushioned protective cover for preventing blisters, pressure sores, abrasions, discomfort, irritation and other injuries to the ears, face and head resulting from the use of ear-mounted, nasal air supply hoses. In particular, the present invention relates to an apparatus and method for protecting the top and back sides of ears and other parts of the face and head of a patient. The protection is intended to prevent development or exacerbation of such injuries due to the continuous and prolonged use of a nasal air supply hose which is worn about the patent's head and face and which is typically supported by draping the hoses about the ears. Use of the present invention also promotes healing of such injuries despite the continued use of such air supply hoses.

2. Description of the Prior Art

Efforts have been made in the past to prevent or facilitate healing of pressure sores, blisters, abrasions, discomfort and other problems associated with the continuous and prolonged use of nasal air supply hoses. Most of such nasal air supply hoses are worn about the head with an air supply cannula assembly disposed below the nasal passage openings. The air supply hoses extend laterally outward from the cannula and are positioned about both sides of the face and head, with one hose on each side. Each hose is draped over the respective top and back of the patients' ears for support. U.S. Pat. No. 3,802,431 to Farr appears to disclose a typical nasal cannula assembly of this type.

One of the many problems associated with the continuous, prolonged use of such a device is the development of pressure sores and abrasions about the top and backs of the patient's ears due to the pressure of the air hose against the patient's sensitive skin. Additionally, the air hoses are usually impervious to moisture. Thus, perspiration and other moisture may build-up on the region of skin beneath the air hose creating an undesirable environment conducive to the development of infection and injury. Also, should this region of sensitive skin atop and behind the ears and elsewhere on the head and face, already be infected, abraded or in a deteriorated condition, the presence of the air hose and resulting lack of exposure to clean, dry air may prevent the proper healing of the skin.

All of these problems create a distressing source of irritation and discomfort to the patient who is already experiencing a medical condition necessitating use of the air supply cannula. Attempts to overcome some of the problems connected with nasal air supply use have led to development of complicated and expensive devices designed to lift the air hose off of the skin at the top and back of the ears. However, such attempts have resulted in creation of headband and face mask configurations which create added expense and difficulties for the patient without any corresponding benefit. U.S. Pat. No. 4,827,923 to Bishop et al. and U.S. Pat. No. 4,739,757 to Edwards appear to disclose such devices.

Other efforts have led to the development of devices which provide a protective covering intended to cushion the area of skin otherwise directly in contact with the air hose so as to minimize the concentration of pressure on the skin and the possibility of injury. Such devices have also attempted to provide a cushion material which allows evaporation of perspiration and other moisture from the skin surface. In an effort to satisfy these objectives, such devices have often been formed from foam-like materials in a thin-sheet or hollow, tubular form. None of the devices previously known have satisfactorily accomplished these objectives. The sheet type devices have been designed to wrap around the air hose to create an outer cushion. These designs have typically increased the stiffness of the air hose resulting in an increased radius of curvature which causes less of the air hose to be in contact with the patient's ear.

The problem with such approaches is that the smaller contact area results in an increased pressure, equal to the weight of the supported air hose, on the patient's skin at the point of contact of the hose and foam-cover combination. This effectively increases the likelihood of pressure sores, abrasions, irritation and discomfort instead of alleviating such problems. Also, the foam materials often disclosed in prior inventions include open-celled, elastomeric foams which do not adequately allow the circulation of fresh air around the air supply hoses and the skin of the patient. Thus, use of such materials creates a dampened, moist environment due to perspiration, bathing of the patient, and moisture from compromised blisters, abrasions and pressure sores, all of which create conditions conducive to serious infection. Such damp or wet skin is more easily injured by the prolonged, continuous use of the air supply hoses. Other devices formed from hollow, tubular foam materials suffer from similar deficiencies. U.S. Pat. No. 4,699,139 to Marshall et. al, U.S. Pat. No. 4,949,733 to Sampson, and U.S. Pat. No. 5,025,805 to Nutter appear to disclose devices of this type.

Patient's whose medical condition necessitates the continuous, prolonged use of ear and head mounted nasal cannula have long been exposed to the risk of serious discomfort, irritation, injury, and unhealing pressure sores resulting from the pressure of air hoses resting against the patient's skin. None of the previous devices have adequately prevented and protected the patient from these problems which gives rise to increased risks of such injuries and problems due to use of nasal air supply hoses. Thus, it is apparent that a need exists for an apparatus and method which not only prevents such problems and injuries but also which protects existing injuries from further injury and irritation and which promotes healing.

SUMMARY OF THE INVENTION

The present invention provides a method and apparatus for protecting the sensitive skin of a patient from discomfort, irritation, and injury associated with the use of ear, head and face-mounted nasal air supply hoses. The invention also promotes healing of injuries associated with the use of such air supply hoses. A generally rectangular, elongated strip of flexible fabric is wrapped around a section of the air supply hose and fastened along overlapping edges of the strip. The flexible fabric incorporates an outer cover of lambs wool or similar material and an inner padding of slightly adhesive or high-friction material, such as a thin layer of latex rubber or releasable adhesive to inhibit longitudinal slippage or movement of the protective cover along the air hose.

The strip of material is supplied either in pre-cut lengths of a predetermined size or as a roll arranged for easy dispensing and convenient storage. Pieces of a desired length can be cut from the roll into predetermined, adjustable lengths, with the remainder conveniently stored for later use. A sufficient length is cut to cover the segment of the air hose which would otherwise be in contact with the sensitive skin of a patient's ear. The roll also is adaptable to incorporate weakened lateral parting lines in the fabric so that a patient or health care worker can manually and conveniently tear off a predetermined length of the material without the need for a cutting or severing tool. The predetermined length of the strip is wrapped around and fastened to the hose along overlapping or confronting longitudinal opposing margins at the side edges of the strip with either hook-and-loop type or adhesive attachment fastening strips. The opposing margins of the strip of material are configured to either overlap or to confront one another such that when the strip is wrapped around the air supply hose, the attachment or fastening strips confront one another and can then be pressed together to releasably fasten the protective cover to the hose.

The protective cover also incorporates a plurality of pairs of release tabs extending from the overlapping edges which are pulled apart to facilitate removal of the cover from the air hose. The pairs of release tabs are spaced apart on the uncut roll of material at predetermined intervals and in such numbers such that at least one pair of release tabs are present on the cut lengths of material.

BRIEF DESCRIPTION OF THE DRAWINGS

Referring now to the drawings wherein like reference numerals across the several different views refer to identical or corresponding parts.

FIG. 7 is a perspective view, in enlarged scale, of the protective cover of FIG. 6 releasably fastened on the air hose;

FIG. 8 is a cross-sectional view, in enlarged scale, taken along section line 8—8 of FIG. 7 with the protective cover releasably secured about the air hose; and FIG. 9 is a perspective view, in reduced scale, of the protective cover of FIG. 6 arranged in a roll prior to dispensing.

DETAILED DESCRIPTION OF THE INVENTION

Figure 1:
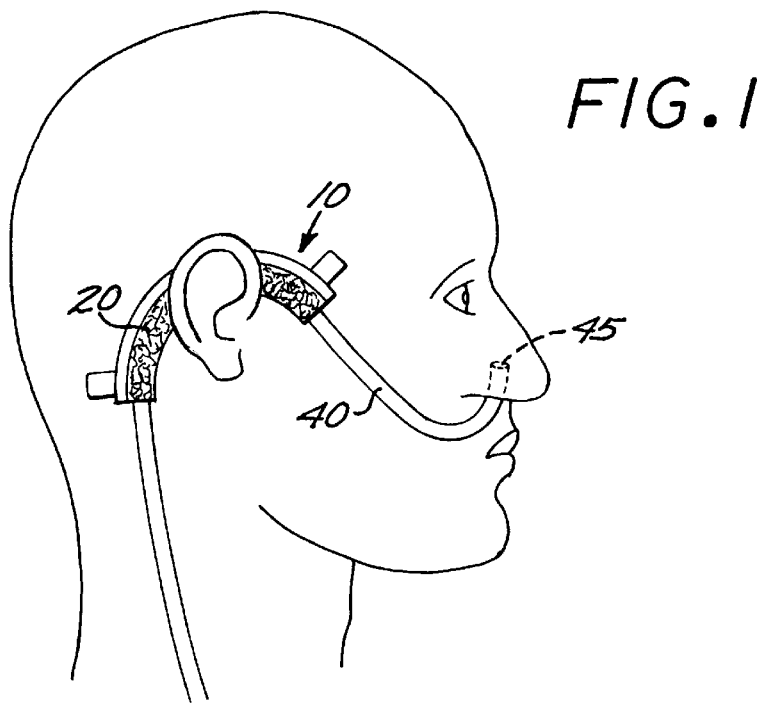
FIG. 1 is a perspective view, in reduced scale, of a cushioned protective cover embodying the present invention as worn by a patient using an ear-mounted, nasal air supply hose.

As shown in the drawings for purposes of illustration, the present invention incorporates a protective cover apparatus which obviates many of the problems associated with the use of ear-mounted nasal air supply hoses in adults, infants and small children having medical conditions requiring the medicinal use of gas supplies such as, for example, pure oxygen. The problems encountered are easily solved by the invention disclosed herein which can be inexpensively manufactured, either in mass quantity or on a custom order basis, from a variety of readily available materials and which is easily affixed to the air supply hoses to provide an air-circulating, moisture evaporating protective cushion around the hose.

One object of this invention is to adequately protect the sensitive skin surrounding the ears, head and face of an adult, infant or young child from discomfort, irritation, infection and injury resulting from the use of the air supply hoses worn by a patient about the top and back of the ears and other parts of the head and face. Such protection is especially intended to eliminate the occurrence of pressure sores, abrasions and similar injuries which are typically associated with use of such hoses.

Another object of the invention is to facilitate and promote the healing of preexisting pressure sores, abrasions and infections resulting from the use of nasal air supply hoses which are worn about the head, face and ears of patients and supported by draping a segment of the hose about the top and back of the patient's ears.

Additional novel features, advantages over previous devices and objects of the inventor will become readily apparent from the embodiments described by the following detailed description of the invention when considered in conjunction with the accompanying drawings.

Referring now to the drawings, the protective cover according to the present invention is illustrated in FIGS. 1–5 and shown generally by reference numeral 10. FIG. 1 reflects the cushioned protective cover 10 fastened to an air hose 40 arranged with a nasal cannula 45 positioned beneath the nasal openings of a patient and with the hose 40 draped about the patient's face and head. A segment of the hose 40 is shown supported by the top and back of the patient's ear. The protective cover 10 incorporates an outer cover 20 of lambs wool (also referred to as "sheep skin") or similar material which rests against the especially sensitive skin surrounding the top and back of the ear. As can be understood from FIG. 2, the protective cover 10 is formed from a strip 15 of generally rectangular and elongated fabric material. As is described in more detail below, the lateral width of such material is preferably of a sufficient width to encircle the predetermined circumference of the outer diameter of the particular air hose 40 in use.

The fabric material of strip 15 consists of any of a wide-variety of readily available loosely woven fabrics including, but not limited to, cotton and similar materials. A loosely woven material is preferable so as to cause air to freely circulate within and around the material in a drying action which is accomplished by absorption, wicking away and evaporation of perspiration and moisture from the skin of the patient. The strip 15 incorporates an outer cover 20 of lambs wool or similar material. The outer cover 20, whether made from lambs wool or a similar material, preferably defines a loosely woven pile of strands configured to allow for the circulation of clean, dry air. The pile is preferably formed with an uncompressed thickness of between approximately one-eight and one-quarter of an inch. Other uncompressed thicknesses work equally well in facilitating air circulation so long as corresponding adjustments are made to the looseness or tightness of the weave to ensure a sufficient amount of cushioning and air circulation. The weave of the strands may be adjusted to accommodate the proper amount of circulation for varying uncompressed thicknesses of the pile. This pile configuration minimizes or completely eliminates the dampened, moist environment which would exist without the protective cover 10. As stated, this environment is typically due to perspiration, bathing of the patient, and moisture from compromised blisters, abrasions and pressure sores, all of which can create conditions conducive to injury and serious infection. Additionally, the pile configuration wicks away and evaporates moisture on the skin and can thereby completely dry otherwise damp or wet skin.

The looseness of the weave of the fabric strip 15 and pile, and the uncompressed thickness of the pile are also important for at least two additional novel functions of the protective cover 10. First, these characteristics impart the proper amount of flexibility to the protective cover 10. The cover 10 must remain at least as flexible as the air hose 40 which is to be covered for the reasons stated below. Secondly, the fabric forming the strip 15 must also be of a relatively loose weave so that it too is, at a minimum, as flexible as the air hose 40 to be covered. This maximized flexibility of the protective cover 10 ensures that its the radius of curvature, and that of the cover 10 and hose 40 combination, is minimized to be no less flexible than the hose 40 itself.

The interior surface 35 of the strip 15 is coated or padded with a high-friction material which is adapted to inhibit longitudinal movement and slippage of the protective cover 10 along the length of air hose 40 during normal use. The material selected to coat the inner surface 35 must be at least as flexible as the materials incorporated for the cover 20, the fabric strip 15 and the air hose 40 for all of the same reasons already stated. The high-friction coating or padding materials preferably include, but are not limited to, latex rubber and releasable adhesives which are applied to the interior surface 35 of the strip 15. Either type of material can be applied to coat or pad either the entire inner surface 35 or just selected portions of the surface 35. As an example for illustration purposes, a releasable adhesive is applied in spaced apart lateral portions of the inner surface 35 so as to save the expense of incorporating unnecessary material while at the same time providing enough of the high-friction material to inhibit the slippage and longitudinal movement of the cover 10 along the air hose 40. Either the latex rubber, releasable adhesive or similar materials are preferably sprayed, sewn or otherwise deposited onto the inner surface 35 of the strip 15 to completely or partially cover surface 35.

As a result of this highly flexible configuration of protective cover 10, a larger segment of the covered air hose rests against the patient's ear, face and head so as to maximize the distribution of weight of the supported air hose 40 across a larger surface area of the patient's skin. This, in turn, minimizes the pressure exerted against the patient's skin at any particular point along the segment of supported air hose 40. The minimized pressure against the patient's skin reduces or altogether eliminates the possibility of discomfort, irritation, blisters, pressure sores, abrasion or other injuries typically associated with the use of such air hoses 40. The combination of the reduced pressure against the skin and the free circulation of air though and around the protective cover 10 offers the patient considerable protection from such problems. Additionally, faster healing is possible when the protective cover 10 of the present invention is used by patients already suffering from such problems even though the patients may be medically required to continue use of the otherwise offending head or ear-mounted nasal air supply hoses 40.

Figure 2:
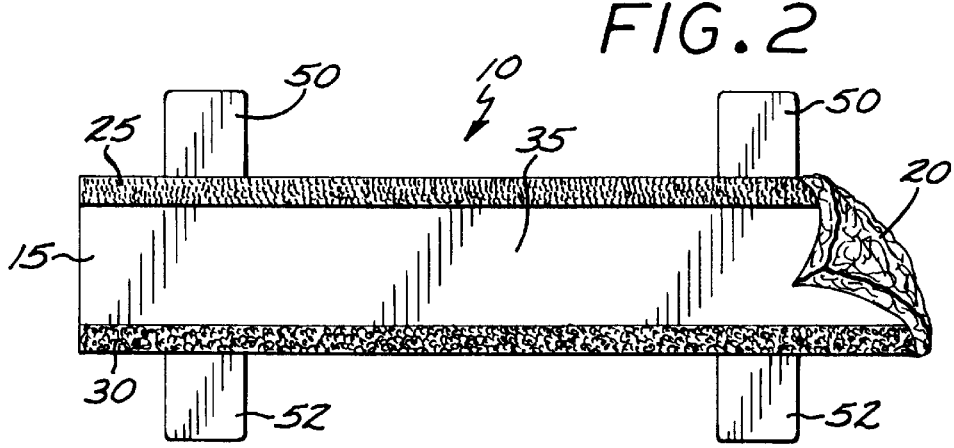
FIG. 2 is a top plan view, in enlarged scale, of the protective cover of FIG. 1.
Figure 3:
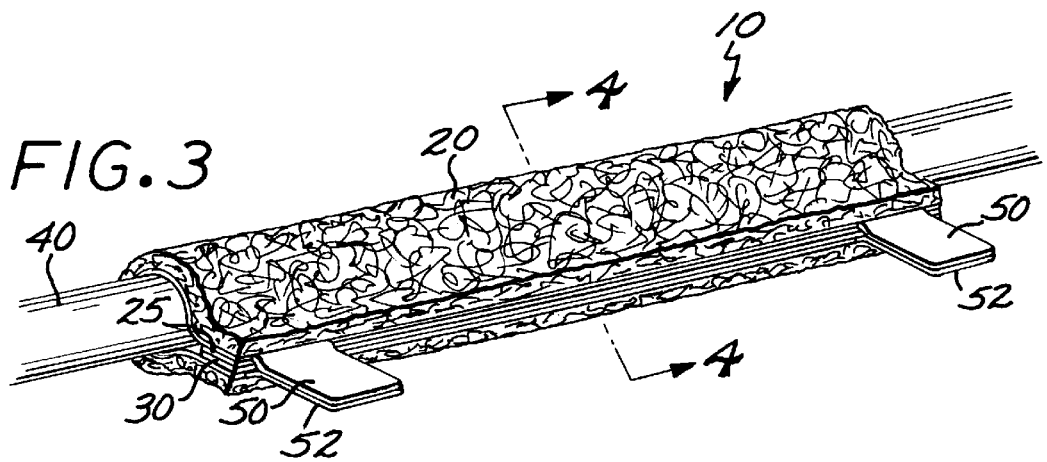
FIG. 3 is a perspective view, in enlarged scale, of the protective cover of FIG. 1 releasably fastened on the air hose.
Figure 4:
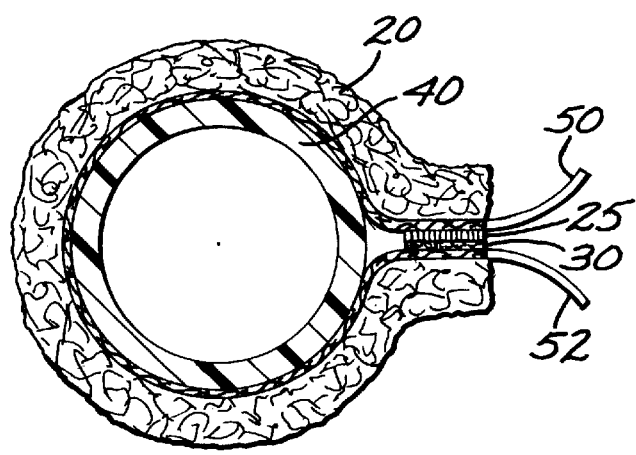
FIG. 4 is a cross-sectional view, in enlarged scale, taken along section line 4—4 of FIG. 3 with the protective cover releasably secured about the air hose.
Figure 5:
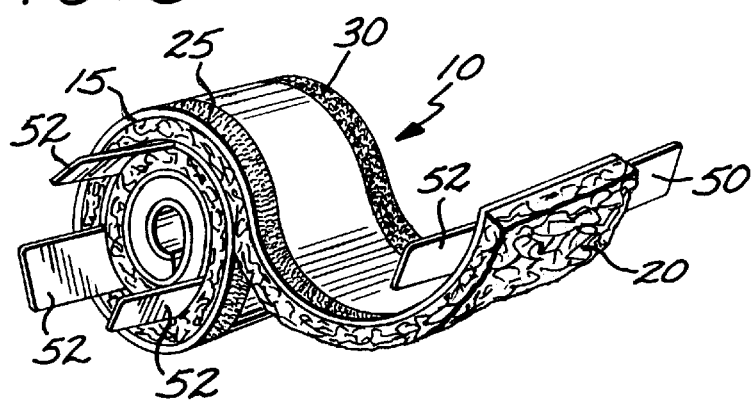
FIG. 5 is a perspective view, in reduced scale, of the protective cover of FIG. 2 and arranged in a roll prior to dispensing.
Figure 6:
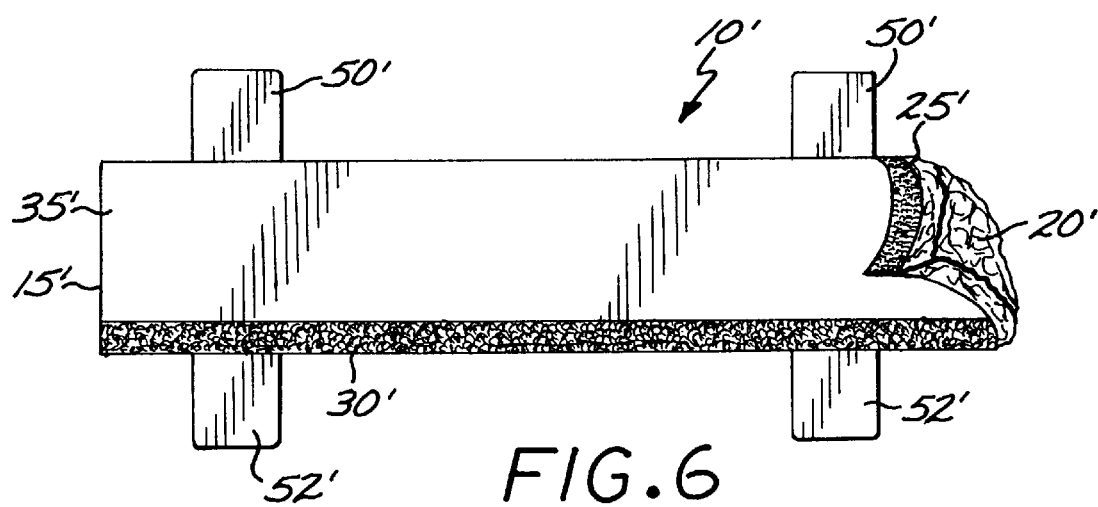
FIG. 6 is a top plan view, in enlarged scale, of an alternative embodiment of the protective cover of FIG. 1.

Still referring to FIG. 2, it can be further understood that the strip 15 incorporates first margin 22 and opposite second margin 23 disposed longitudinally along the opposite edges of strip 15. In this particular embodiment, margins 22, 23 are preferably approximately one-eighth of an inch each and incorporate thereon, first and second attachment or fastening strips 25 and 30, respectively. When the strip 15 is wrapped around the air hose 40, as will be apparent with reference to FIG. 3, the opposite margins 22, 23 extend laterally from the strip 15 in a confronting relationship. In this configuration, the first and second attachment strips 25, 30 are then pressed together to releasable fasten the strip 15 to the hose 40. The attachment strips 25, 30 are preferably formed either with a hook and loop type material such as, e.g., Velcro, or with any of a wide-variety of well-known releasable adhesives.

As briefly described above, the strip 15 is formed with a predetermined lateral width sufficient to completely surround the air hose 40. Ear-mounted nasal air supply hoses most commonly in use have a predetermined diameter of approximately one-eighth inch. The predetermined circumference is calculated by multiplying the predetermined diameter of the air hose 40 by the conversion factor (commonly referred to as pi) which is approximately equal to 3.14. Thus, including the laterally extending margins 22, 23 of approximately one-eighth of an inch each, the total lateral width of the strip 15 for this particular embodiment is preferably approximately 3.14 times the diameter of the air hose 40 or approximately 1.10 inches wide, excluding applicable manufacturing tolerances ranging approximately from one-sixteenth to one-eighth of an inch. For air hoses 40 having an approximate diameter of one-quarter of an inch, the lateral width is preferably approximately 1.60 inches wide, excluding the applicable manufacturing tolerances stated above.

As is most easily understood from FIGS. 2–5, the strip 15 is also formed with one or more pairs of flexible release tabs 50, 52 extending laterally from the edge of the margins 22, 23. Each pair, if more than one, are spaced apart in a longitudinal direction along the edge of the margins 22, 23. In order to facilitate the removal of the strips 15 from the air hoses 40, the release tabs 50, 52 are pulled apart in opposite directions to create an initial separation of the strip 15. The remainder of the attachment strips 25, 30 are then more easily peeled apart from one another to completely remove the protective cover 10. In this manner, the protective cover 10 is removed to allow replacement with a new cover 10 in the event the air hoses 40 are to be reused. The cover 10 is replaced when it becomes soiled, dampened or otherwise unserviceable due to bathing of the patient, drainage from previous infections, pressure sores, burst blisters, abrasions or other injuries. The cover 10 is also replaced when the pile of the outer cover 20, 20' has become permanently matted or compressed due to excessive wetness and or continuous, prolonged use by the patient such that it no longer provides the desired cushioning, weight distribution and air circulation. Embodiments of the present invention incorporating release tabs 50, 52 are particularly suitable for increasing the convenience to patients and health care personnel experiencing arthritic conditions, dexterity impairments or other weaknesses in the hands and fingers. While the tabs 50, 52 are preferably sized large enough for convenient gripping, their size is also minimized so as to lessen any possible discomfort to the patient. Also, the tabs 50, 52 are preferably made from a soft, flexible cotton or similar material to further minimize or eliminate any annoyance or discomfort to the patient.

As can be understood from FIGS. 6–9, an alternative embodiment of the protective cover is disclosed and designated generally by reference numeral 10'. In these figures, like numerals represent like or similar elements as previously described above. In this particular embodiment, as can be understood with reference to FIG. 8, margins 25', 30' are positioned on opposite sides 20' and 35' of strip 15' and the lateral width of the strip 15' is modified such that the margins 22', 23' overlap when strip 15 is wrapped around air hose 40. In this configuration, attachment strips 25' and 30' are positioned on the margins 22', 23' as with the previously described embodiment such that the attachment strips 25' and 30' are positioned in a confronting relationship. As with the previously described embodiment, the attachment strips 25' and 30' are pressed against one another to fasten the protective cover 10' to the air hose 40'. Incorporation of the unique features of this particular embodiment is contemplated for each of the other variations described herein.

In each of the above-described embodiments, the protective cover apparatus 10 can be manufactured either in pre-cut strips 15 of a predetermined length, see for example FIGS. 2, 3, 6 and 7, or in a roll configuration 12, 12'. See, for example, FIGS. 5 and 9. In the precut configuration of strip 15, the predetermined length is preferably approximately three inches. This predetermined length is approximately equal to the length needed to protect, cushion and cover the patient's sensitive skin which covers the top and back of the ears of the average adult patient. This predetermined length is adjustable to be longer or shorter to accommodate protection and coverage of other parts of the head and face, including, but not limited to, the jawline, cheeks and upper lip. Other pre-cut lengths suitable for use with larger or smaller adults, children and infants having varied head, face and ear anatomy are also contemplated by the present invention. As an alternative to the pre-cut cover 10 of a predetermined length, the above-described protective covers 10 and 10' can be fabricated in a roll configuration 12, 12', for easy dispensing and convenient storage. See, for example, FIGS. 5 and 9.

In the roll configuration 12, 12', the protective covers 10, 10' are preferably formed to have the desired, predetermined length by unrolling a selected portion of the strips 15, 15' from the roll 12, 12' and cutting and severing with scissors or other cutting tool the predetermined length of the protective covers 10, 10' from the roll 12, 12'. More preferably, the strips 15, 15' are configured on the roll 12, 12' to include longitudinally spaced apart weakened, lateral parting lines 14, 14' adapted to enable easy, manual separation of the predetermined length of strip 15 from the roll 12, 12'. In the preferred embodiment, the strips 15, 15' in the roll configuration are laterally pre-scored or otherwise weakened, at equal, spaced apart longitudinal distances equal to the predetermined distance of approximately three inches. As before, the predetermined distance is adjustable to accommodate the head, face and ear anatomy of particular patients. With this configuration, protective covers 10, 10' are quickly and efficiently separable from the roll 12, 12' without the need for cutting and severing tools. The non-scored embodiment is preferable for applications involving use of the protective covers 10, 10' with a variety of patients for whom various lengths are needed. Incorporation of the pre-scored or otherwise weakened lateral parting lines 14, 14' into any of the above embodiments are especially suitable for use of the protective covers 10, 10' in a convenient roll configuration by patients and health care personnel experiencing arthritic conditions, dexterity impairments or other weaknesses in the hands and fingers.

All of the above-illustrated embodiments contemplate selection of medical grade fabric strips 15, 15', outer covers 20, 20', and attachment strip 25, 25', 30, 30' materials which are compatible for manufacture and sale as sterilized and unsterilized strips of predetermined length or in the roll configuration 12, 12'.

A method for using the above-described embodiments of the protective cover 10, 10' as described herein and in the accompanying drawings and figures is also contemplated by the present invention. Initially, the ear-mounted nasal air supply hose 40 is selected for use with a particular patient. Next, a particular configuration of the protective covers 10, 10' is selected which incorporates a predetermined longitudinal length and width, an outer cover of lambs wool or similar material 20, 20', an inner high-friction surface material 35, 35', opposing first and second margins 22, 22', 23, 23' and first and second attachment strips 25, 25', 30, 30'.

Next, a segment of the protective cover 10, 10' formed in the roll configuration 12, 12' is extended or dispensed from the roll 12, 12'. A predetermined length of the protective cover 10, 10' is then separated from the roll 12, 12'. For the embodiments incorporating the pre-scored or weakened parting line 14, 14', the strip 15, 15' is manually separated from the remainder of the roll 12, 12'. Otherwise, the predetermined length of strip 15, 15' is cut and severed from the roll 12, 12' using a pair of scissors or other cutting tool. The protective cover 10, 10' is then wrapped around the segment of the air hose 40, 40' with either margins 22, 23 extending laterally from strip 15 or with margins 22', 23' overlapping one another on strip 15'. In either embodiment, first and second attachment strips 25, 25', 30, 30' are pressed against one another to fasten the protective cover 10, 10' to the segment of the air hose 40 to come in contact with a region of the patient's sensitive skin.

With the protective cover 10, 10' affixed to the air hose 40, the ear-mounted nasal air supply cannula 45 is inserted into the nasal passages and the air hose 40 is donned about the head, face and ears of the patient. The protective cover 10, 10' is removed and replaced by pulling the tabs 50, 50', 52, 52' apart in opposite directions and then peeling the attachment strips 25, 25', 30, 30' apart from one another until the protective cover 10, 10' is fully separated from the air hose 40. A new protective cover 10, 10' is fastened to the air hose using the above-described steps to replace an old cover 10, 10' which has become soiled, dampened or otherwise unserviceable due to bathing of the patient, infection drainage from previous sores, burst blisters, abrasions or other injuries, or when the pile of the outer cover 20, 20' has become permanently matted or compressed due to continuous, prolonged use by the patient such that it no longer provides the desired cushioning, weight distribution and air circulation.

Each of the above-described various embodiments and configurations of the present invention are combinable in any of a large number of comparable and similar variations and configurations without departing substantially from the scope of the invention. Many of the above-described embodiments and configurations have been described with specific reference to ear-mounted nasal air supply hoses. However, the invention is equally suitable for solving the same types of problems associated with the use of other various types of head and face mounted air supply devices. Similarly, the invention is easily configured for use with medicinal fluid administration devices configured for use elsewhere on the body of a patient including, but not limited to, the ears, head and face.

The preceding description of the preferred embodiments and the best mode for practicing the invention are provided for illustration purposes only and not for the purpose of limitation; the invention being defined by the claims.

I claim:

1. A cushioned protective cover for preventing discomfort, irritation, blisters, pressure sores, abrasions and other injuries to a patient resulting from use of an ear-mounted, nasal air supply hose having a predetermined circumference, comprising:

an elongated flexible strip of fabric configured to permit dispensing of a selectable length of said strip and said selected length further including an outer cover of lambs wool defining a pile of strands configured to allow for circulation of air, an interior surface of high-friction material adapted to inhibit longitudinal movement along the air hose, first and second opposite margins and with said strip being formed with a lateral width large enough to allow said strip to be wrapped around the circumference of the air hose; and first and second releaseable attachment strips on the respective said first and second margins confronting one another and releaseably attaching together when said strip is wrapped around the air hose.

2. The protective cover of claim 1, wherein:

said lambs wool covering is configured with a loosely woven pile having an uncompressed thickness of approximately between one-eighth and one-quarter of an inch.

3. The protective cover of claim 1, wherein:

the respective said first and second attachment strips are disposed on said margins on the interior surface of said flexible strip, and said first and second margins depend laterally therefrom such that said attachment strips confront one another and releasably attach together when said flexible strip has been wrapped around the air hose.

4. The protective cover of claim 1, wherein:

said first attachment strip is disposed on said first margin on said outer cover side of said flexible strip and said second attachment strip is disposed on said second margin on said interior surface such that the respective said first and second attachment strips overlap in a confronting relationship and releasably attach together.

5. The protective cover of claim 1, further comprising:

at least one pair of release tabs disposed along an edge of said opposite margins and projecting laterally therefrom and sized to allow easy separation of said attachment strips.

6. The protective cover of claim 1, wherein:

said first and second releasable attachment strips include respective portions of hook and pile material adapted to releasably hook together.

7. The protective cover of claim 1, wherein:

said first and second releasable attachment strips include respective portions of releasable, medical grade adhesive adapted to releasably fasten said strips together.

8. The protective cover of claim 1, wherein:

said elongated flexible strip is arranged in a roll for dispensing selectable lengths.

9. The protective cover of claim 8, wherein:

said flexible strip incorporates a plurality of weakened lateral parting lines longitudinally spaced apart at predetermined distances with said parting lines configured for manual separation from said roll of a length of said strip equal to said predetermined distance.

10. The protective cover of claim 1, wherein:

said flexible strip incorporates a plurality of weakened lateral parting lines longitudinally spaced apart at predetermined distances with said parting lines configured for customization of the length of said strip by manual separation of said strip at said predetermined distances.

11. The method as set forth in claim 10, whereby:

said flexible strip incorporates a plurality of weakened lateral parting lines longitudinally spaced apart at predetermined distances with said parting lines configured for customization of the length of said strip by manual separation of said strip at said predetermined distances.

12. A cushioned protective cover for preventing discomfort, irritation, blisters, pressure sores, abrasions and other injuries to a patient resulting from use of an ear-mounted, nasal air supply hose having a predetermined circumference, comprising:

a roll of elongated flexible fabric capable of dispensing in a selected strip and said strip configured to include an outer cover of absorbent material defining a pile of strands configured to allow for circulation of air, an interior surface of high-friction material adapted to inhibit longitudinal movement along the air hose, first and second opposite margins and with said strip being formed with a lateral width large enough to allow said strip to be wrapped around the circumference of the air hose; and first and second releaseable attachment strips on the respective said first and second margins confronting one another and releaseable attaching together when said flexible strip is wrapped around the air hose.

13. The protective cover of claim 12, wherein:

said flexible strip incorporates a plurality of weakened lateral parting lines longitudinally spaced apart at predetermined distances with said parting lines configured for manual separation from said roll of a length of said strip equal to said predetermined distance.

14. A method for using a cushioned protective cover adapted for preventing discomfort, irritation, blisters, pressure sores, abrasions and other injuries to a patient resulting from use of an ear-mounted nasal air supply hose having a predetermined circumference, comprising:

selecting a roll of an elongated flexible strip of fabric configured to include an outer cover of lambs wool defining a pile of strands configured to allow for circulation of air, an interior surface of high-friction material adapted to inhibit longitudinal movement along the air hose, first and second opposite margins and with said strip being formed with a lateral width large enough to allow said strip to be wrapped around the circumference of the air hose, and first and second releasable attachment strips on the respective said first and second margins confronting one another and releasably attaching together when said flexible strip is wrapped around the air hose;

dispensing a portion of said flexible strip from said roll;

separating a selected length from said portion; and wrapping said selected length about an ear-mounted nasal air supply hose.

15. The method of claim 14, wherein:

said separating step further comprises cutting and severing said predetermined length from said portion.

16. The method of claim 14, wherein:

said first margin is disposed about an edge of said outer cover and said second margin is disposed about an edge of said inner surface such that the respective said first and second margins overlap one another when said strip is wrapped around the hose, and wherein said wrapping step further comprises fastening the respective said first and second attachment strips together by pressing them against one another.

17. The method of claim 14, wherein:

the respective said first and second opposite margins project laterally from said strip in a confronting relationship when said strip is wrapped around the hose, and wherein said wrapping step further comprises fastening the respective said first and second attachment strips together by pressing them against one another.

18. A method for using a cushioned protective cover adapted for preventing discomfort, irritation, blisters, pressure sores, abrasions and other injuries to a patient resulting from use of an ear-mounted nasal air supply hose having a predetermined circumference, comprising:

selecting an elongated flexible strip of fabric configured to include an outer cover of lambs wool defining a pile of strands configured to allow for circulation of air, an interior surface of high-friction material adapted to inhibit longitudinal movement along the air hose, first and second opposite margins and with said strip being formed with a lateral width large enough to allow said strip to be wrapped around the circumference of the air hose, and first and second releaseable attachment strips on the respective said first and second margins confronting one another and releaseably attaching together when said flexible strip is wrapped around the air hose, said strip being further configured to permit dispensing at customized lengths;

determining the desired length for said strip so as to cover the portions of the air hose which are in contact with the patient's ears and cheek;

dispensing said strip to the desired length;

applying said strip of fabric about an ear-mounted nasal air supply hose; and securing said strip of fabric by attaching said first margin to said second margin by applying pressure to said margins thereby securing said releaseable strips.

19. A cushioned protective cover for preventing discomfort, irritation, blisters, pressure sores, abrasions and other injuries to a patient resulting from use of an ear-mounted nasal air supply hose having a predetermined circumference, comprising:

a roll of an elongated flexible strip of fabric configured to include an outer cover of lambs wool defining a pile of strands configured to allow for circulation of air, an interior surface of high-friction material adapted to inhibit longitudinal movement along the air hose, first and second opposite margins and with said strip being formed with a lateral width large enough to allow said strip to be wrapped around the circumference of the air hose, and first and second releaseable attachment strips on the respective said first and second margins confronting one another and releaseably attaching together when said flexible strip is wrapped around the air hose; and said strip being formed with parting lines spaced along the length thereof to for therebetween selected lengths so said strip may be unrolled from said roll and selected lengths separated therefrom along said parting lines, said separated selected lengths to be wrapped about an ear-mounted nasal air supply hose.

* * * * *